United States Patent [19]

Lee

[11] 4,072,056
[45] Feb. 7, 1978

[54] FLUID CONTAINMENT STRUCTURE FOR TRANSDUCER SYSTEM

[75] Inventor: Arnold St. Jacques Lee, Portola Valley, Calif.

[73] Assignee: Varian Associates, Inc., Palo Alto, Calif.

[21] Appl. No.: 700,269

[22] Filed: June 28, 1976

[51] Int. Cl.$^2$ .............................................. G01L 7/08
[52] U.S. Cl. ............................. 73/706; 128/2.05 D
[58] Field of Search ................. 73/395, 406, 407 R; 128/2.05 D; 92/104, 101; 338/42

[56] References Cited

U.S. PATENT DOCUMENTS

| | | | |
|---|---|---|---|
| 2,913,008 | 11/1959 | Cordero | 92/104 |
| 3,079,953 | 3/1963 | Mounteer | 92/104 |
| 3,131,638 | 5/1964 | Wilson et al. | 92/5 R |
| 3,818,765 | 6/1974 | Eriksen | 73/395 |

Primary Examiner—James J. Gill
Assistant Examiner—Anthony V. Ciarlante
Attorney, Agent, or Firm—Stanley Z. Cole; Leon F. Herbert

[57] ABSTRACT

Pressure transducer apparatus primarily for medical use in determining the hemodynamic pressure associated with circulation of the blood. The pressure transducing wall is in contact with a highly compliant diaphragm wall of a fluid container adapted for connection to a patient's blood system. In order to prevent distortion in the blood pressure wave as it is transmitted through the container diaphragm wall to the transducing wall, means are provided for venting air trapped between the diaphragm and the transducing wall.

8 Claims, 2 Drawing Figures

FLUID CONTAINMENT STRUCTURE FOR TRANSDUCER SYSTEM

BACKGROUND OF THE INVENTION

The invention is particularly designed for use in the medical field and more particularly for use in the field of detecting hemodynamic pressure.

Prior to the invention it has been customary to measure hemodynamic pressure by connecting a conduit from a blood vessel in a living being to the pressure sensitive wall of a tranducer. The result is that the transducer detects the blood pressure waves. In order to obtain the required sterile conditions, it is necessary to sterilize all surfaces in contact with the fluid connection to the blood system and it is also necessary that such surfaces be of a material which will not introduce objectionable elements to the blood system. Where the fluid containment structure includes the wall of the transducer, so that the fluid contacts the transducer, the transducer must be sterilized after each use. Also it is difficult to make a suitable fluid-tight connection between the conduit and the transducer. Attempts have been made to construct the fluid containment system separate from the transducer and have a diaphragm wall of the fluid containment structure positioned for contact with the transducer wall. This approach would solve the noted problems, but it has not been successful because it has been found that the blood pressure wave is not faithfully transmitted through the diaphragm to the transducer reliably, unless the space between the diaphragm wall and the transducer wall be filled with liquid.

SUMMARY OF THE INVENTION

According to the present invention it has been found that the reason for failure of prior attempts to make a fluid containment structure separate from the transducer without liquid coupling is that when the fluid containment diaphragm is placed against the transducer, gas (air or any other gas) is trapped between the two surfaces and interferes with the precise transmission of the blood pressure wave. The invention solves this problem by providing means for venting gas from the space between the fluid containment diaphragm and the pressure-sensitive wall of the transducer.

Accordingly, an object of the invention is to provide a hemodynamic pressure detecting apparatus which is accurate and yet has a fluid containment structure which is separate from the transducer. In this way, the fluid containment structure can be sterilized alone and there is no need to sterilize the transducer or be concerned about the materials used in the pressure sensitive wall of the transducer. Since the fluid containment structure is inexpensive compared to the transducer, the fluid containment structure may even be thrown away after one use.

DETAILED DESCRIPTION OF THE INVENTION

Figure 1:
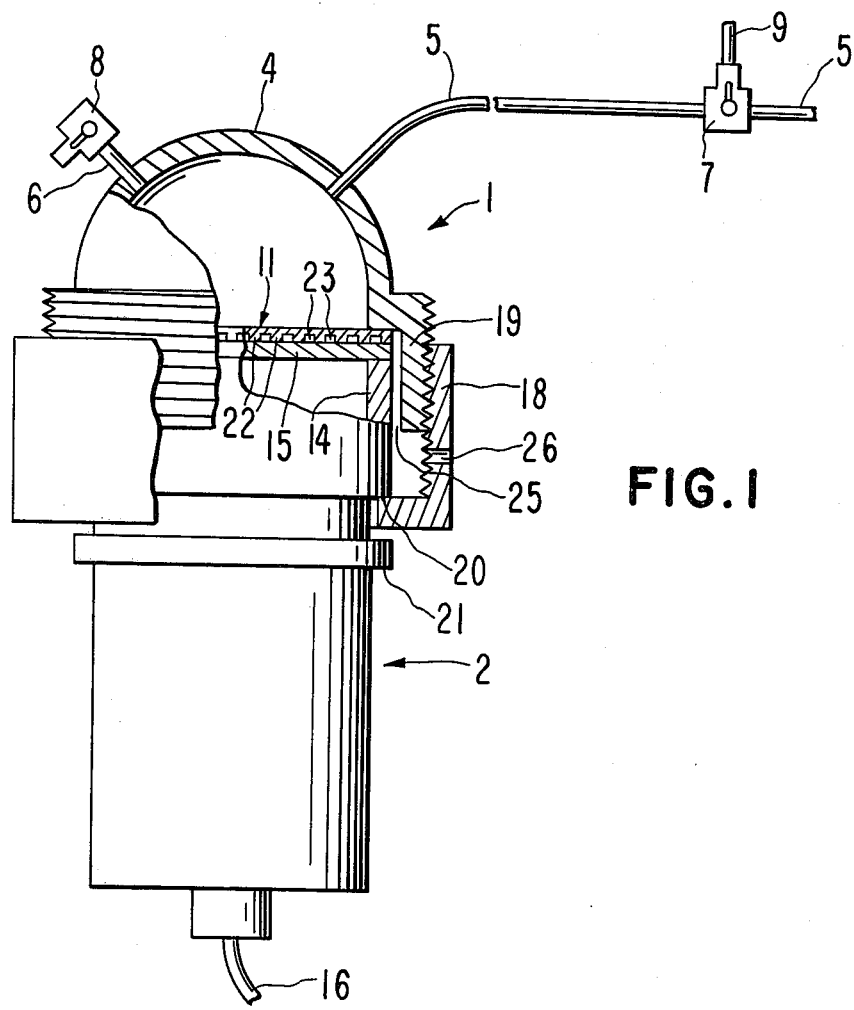
FIG. 1 is an elevational view partly in section showing the separate fluid containment structure held in place on the transducer.
Figure 2:
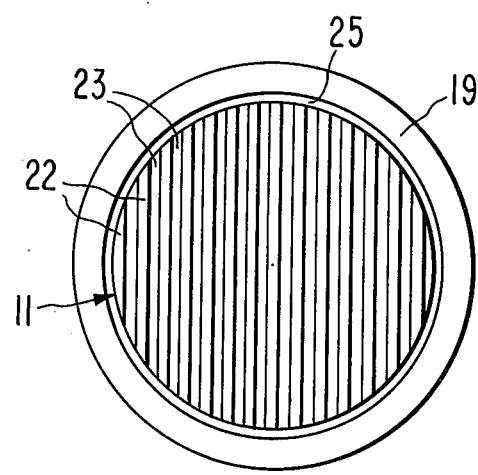
FIG. 2 is a bottom view of the diaphragm end wall of the fluid containment structure.

As shown in the drawings, the apparatus for detecting hemodynamic pressure comprises a separate fluid containment structure 1 connected to a pressure transducer 2. The fluid containment structure comprises a main body portion 4 which is preferably dome shaped as shown in the drawings. The main body 4 has at least one, and preferably two flexible tubes 5 and 6 connected thereto. Each of the tubes is provided with a conventional three-way valve as indicated at 7 and 8. In conventional operation the valve 8 is used to admit atmospheric pressure for obtaining a zero setting for the apparatus. Tube 5 is connected to the blood system of the patient, and valve 7 permits the attendant to fill the containment structure with liquid such as 0.9% NaCl solution through a side tube 9.

The main body 4 includes a diaphragm end wall 11. The main body 4 and the associated tubing must be of nondistensible construction to avoid attenuating the blood pressure wave, and the diaphragm 11 must be very compliant in order to faithfully transmit the blood pressure wave to the transducer. By way of example the main body 4 can be made of thick plexiglass and the diaphragm 11 can be made of a thin sheet of polyparaxylylene bonded to the main body 4 with a silicone adhesive.

The transducer 2 is a conventional transducer such as Model No. P23DB made by Statham Instrument Division of Gould Company. The transducer has a cylindrical outer wall 14, a pressure-sensitive transducing wall 15 and an electrical lead 16. As is well known in the art, pressure variations against the outer surface of wall 15 will cause electrical output signals from the transducers which signals are representative of the instantaneous pressure against the outer surface of wall 15. The dome-shaped body 4 is held in place on the transducer by a circular nut 18 having a threaded engagement with threads on a downwardly projecting cylindrical wall 19 of the transducer dome. Upward movement of nut 18 is limited by engagement with an annular lip 20 on the transducer, and the nut is prevented from slipping off the transducer by a ring 21 attached to the transducer.

In operation, the dynamic pulse wave as well as the static pressure from the blood system of the patient to which tubing 5 is connected will be transmitted through tubing 5 into the dome shaped body 4 and against the inner surface of diaphragm 11. Since diaphragm 11 responds to pressure in the body 4 with substantially no resistance, diaphragm 11 transmits the blood pressure to the outer surface of pressure sensitive wall 15 of the transducer. According to the invention, it has been found that if the outer surface of diaphragm 11 is flat, gas tends to become trapped between the diaphragm and the pressure sensitive transducer wall 15. It has also been found that such trapped gas causes inaccurate electrical output from the transducer. In accordance with the invention, the problem is solved by venting the interface between diaphragm 11 and wall 15 to remove or substantially reduce the possibility of trapped gases. In a preferred embodiment the venting is accomplished by making the outer surface of diaphragm 11 microscopically corrugated or ridged as shown at 22 so that a network of passages or grooves 23 are provided to vent gas to the atmosphere.

Although diaphragm 11 is drawn relatively thick in order to show its detailed construction, it is intended to be very thin. For example, diaphragm 11 may have a total thickness on the order of 0.005 inch, and the depth of the grooves 23 may be on the order of 0.002 inch. The main considerations are that the diaphragm be sufficiently compliant to offer substantially no resistance to transmission of pressure in dome 4 to the surface of transducer wall 15; and at the same time the material of diaphragm 11 must be sufficiently non-compressible to prevent attenuating the pulse and to prevent collapse of the ridges 22 which would close the gas passages 23. In order to avoid the possibility that gas passing out of grooves 23 will be trapped by dome wall 19 and thus prevent sufficient venting, the inner diameter of wall 19 is larger than the outer diameter of diaphragm 11 to provide an annular passage 25. Similarly, nut 18 is preferably provided with one or more ports 26 for unrestricted venting.

Although the grooves or passages 23 are shown to be all parallel and extending in only one direction, they obviously could be in the form of grooves across the face of diaphragm 11 in two directions at right angles to each other or take other appropriate network form. Also it should be understood that the outer surface of wall 15 could be grooved instead of grooving the surface of wall 11, or they could both be grooved. Similarly, the grooves could be formed by bonding narrow spaced strips of material to the facing surfaces of one or both of the walls 11 and 15 rather than by forming the grooves integrally in the diaphragm 11 as shown. Alternatively the passages could be formed by many spaced bumps instead of continuous ridges. Also, the venting passages could be formed on both sides of a separate compliant sheet placed between wall 15 and diaphragm 11.

While there have been described and illustrated specific embodiments of the invention, it will be clear that variations in the details may be made without departing from the true spirit and scope of the invention as defined in the appended claims and their legal equivalents. For example, it should be understood that while the invention is specifically described in connection with a system for measurement of hemodynamic pressures, it can be utilized in any fluid pressure detecting system. Similarly, it should be understood that the invention is applicable to systems in which the pressure variations originate in the transducer and would then be transmitted through diaphragm 11 to fluid in the container 4 in any situation in which it is desired to create pressure waves in a fluid system.

What is claimed is:

1. In pressure transducer apparatus comprising a pressure transducer having a pressure transducing wall and means for providing an electrical output representative of pressure exerted against said wall, wall means forming a structure for containing fluid for pressure interaction with said transducer wall without direct contact between the fluid and said transducer wall, said fluid containment structure having a diaphragm wall positioned for contact with said transducer wall, said diaphragm wall being sufficiently compliant to provide transmission between fluid pressure in said containment structure and said transducer wall; the improvement wherein means are provided for venting gas from between said diaphragm wall and said transducer wall.

2. Apparatus as claimed in claim 1 wherein said venting means comprises gas passageways extending across the diaphragm surface facing said transducer wall.

3. Apparatus as claimed in claim 2 wherein said fluid containment structure is detachably secured to said transducer by means which provide for venting gas from said passageways to the atmosphere.

4. Apparatus as claimed in claim 1 in which said fluid containment structure comprises a dome shaped main body having at least one tubing connected thereto, and said diaphragm forms the end wall of said dome shaped body.

5. Apparatus as claimed in claim 1 wherein said transducing wall is integral with said transducer and said diaphragm wall is integral with said fluid containment structure, whereby said fluid containment structure can be removed from said transducer and disposed of or sterilized independent of said transducer.

6. Apparatus as claimed in claim 5 wherein said venting means comprises raised and recessed portions on the outer surface of said diaphragm wall, and the distance between adjacent raised portions is substantially the same at all locations on the diaphragm wall.

7. A fluid containment structure for use with transducers, said containment structure comprising wall means for confining fluid therein, said wall means having a portion thereof in the form of a compliant diaphragm responsive to fluid pressures in said containment structure for transmitting such pressures by contact with a transducer, and means on the outer surface of said diaphragm forming passages for venting gas from substantially all areas of the diaphragm to the periphery of said diaphragm at a plurality of locations around said periphery.

8. Apparatus as claimed in claim 7 wherein said passage forming means comprises raised and recessed portions on said diaphragm, and the distance between adjacent raised portions is substantially the same at all locations on the diaphragm.

* * * * *